US012567152B2

(12) United States Patent (10) Patent No.: US 12,567,152 B2
Kweon et al. (45) Date of Patent: Mar. 3, 2026

(54) BLOOD VESSEL IMAGE SEGMENTING METHOD AND APPARATUS USING PLURALITY OF PREDICTION RESULTS

(71) Applicant: MEDIPIXEL, INC., Seoul (KR)

(72) Inventors: Ji Hoon Kweon, Seoul (KR); Young Hak Kim, Seoul (KR); Hwi Kwon, Seoul (KR)

(73) Assignee: MEDIPIXEL, INC., Seoul (KR)

( * ) Notice: Subject to any disclaimer, the term of this patent is extended or adjusted under 35 U.S.C. 154(b) by 349 days.

(21) Appl. No.: 18/202,369

(22) Filed: May 26, 2023

(65) Prior Publication Data

US 2023/0298180 A1 Sep. 21, 2023

Related U.S. Application Data

(63) Continuation of application No. PCT/KR2021/014303, filed on Oct. 15, 2021.

(51) Int. Cl.
*G06T 7/11* (2017.01)
*A61B 6/50* (2024.01)
*G06T 7/136* (2017.01)

(52) U.S. Cl.
CPC ............... *G06T 7/11* (2017.01); *A61B 6/504* (2013.01); *G06T 7/136* (2017.01); *G06T 2207/30101* (2013.01)

(58) Field of Classification Search
CPC ....... A61B 6/481; A61B 6/504; A61B 6/5217; G06T 7/11; G06T 7/136; G06T 2207/10116; G06T 2207/20081; G06T 2207/30101; G16H 30/40; G16H 50/20
See application file for complete search history.

(56) References Cited

U.S. PATENT DOCUMENTS

| | | |
|---|---|---|
| 7,644,072 B2 | 1/2010 | Budzik et al. |
| 10,524,755 B2 | 1/2020 | Kowarschik et al. |
| 2011/0194776 A1* | 8/2011 | Nakamura ................ G06T 7/60 |
| | | 382/195 |

(Continued)

FOREIGN PATENT DOCUMENTS

| | | |
|---|---|---|
| JP | 2009504297 A | 2/2009 |
| JP | 5801226 B2 | 10/2015 |

(Continued)

OTHER PUBLICATIONS

Fraz et al. "An ensemble classification-based approach applied to retinal blood vessel segmentation." IEEE Transactions on Biomedical Engineering 59.9 (2012): 2538-2548. (Year: 2012).*

(Continued)

*Primary Examiner* — Katrina R Fujita
(74) *Attorney, Agent, or Firm* — BOND, SCHOENECK & KING, PLLC; George R. McGuire

(57) ABSTRACT

A blood vessel image segmentating method according to an embodiment may comprise the steps of: generating a plurality of candidate mask images regarding a target blood vessel by applying a plurality of blood vessel segmentation models on a blood vessel image; evaluating an error level for each of the generated plurality of candidate mask images; and generating a target blood vessel segmentation result from the candidate mask images, on the basis of the evaluated error level.

11 Claims, 12 Drawing Sheets

(56)                    References Cited

U.S. PATENT DOCUMENTS

| | | | | |
|---|---|---|---|---|
| 2014/0294235 A1* | 10/2014 | Ishida | ......... | G06V 40/193 |
| | | | | 382/103 |
| 2016/0110874 A1* | 4/2016 | Matthews | ......... | G06T 7/174 |
| | | | | 382/131 |
| 2016/0328855 A1 | 11/2016 | Lay et al. | | |
| 2018/0366225 A1* | 12/2018 | Mansi | ......... | G16H 40/20 |
| 2019/0355120 A1 | 11/2019 | Wang | | |
| 2020/0202527 A1* | 6/2020 | Choi | ......... | G06T 5/73 |
| 2021/0350529 A1* | 11/2021 | Ayinde | ......... | G06N 20/20 |
| 2023/0162359 A1* | 5/2023 | Choi | ......... | G16H 50/20 |
| | | | | 382/128 |

FOREIGN PATENT DOCUMENTS

| | | |
|---|---|---|
| JP | 2019521733 A | 8/2019 |
| KR | 20110065709 A | 6/2011 |
| KR | 20110077740 A | 7/2011 |
| KR | 20170126262 A | 11/2017 |
| KR | 20200005404 A | 1/2020 |
| KR | 20200093502 A | 8/2020 |
| KR | 20210149350 A | 12/2021 |
| KR | 102521660 B1 | 4/2023 |

OTHER PUBLICATIONS

Geetharamani et al. "Retinal blood vessel segmentation employing image processing and data mining techniques for computerized retinal image analysis." Biocybernetics and Biomedical Engineering 36.1 (2016): 102-118. (Year: 2016).*

Hann, Evan. Deep ensemble learning-based quality control for automatic segmentation in cardiovascular magnetic resonance imaging. Diss. University of Oxford, 2020. (Year: 2020).*

International Search Report and Written Opinion of PCT/KR2021/014303, filed Oct. 15, 2021. Mailing date of Search Report—Mar. 10, 2022, pp. 1-6.

* cited by examiner

From 310

Hole filling of candidate mask image ~410

Remove blob including number of pixels equal to or less than first threshold number from areas indicating target blood vessel in candidate mask image ~420

To 320

600

700

900

BLOOD VESSEL IMAGE SEGMENTING METHOD AND APPARATUS USING PLURALITY OF PREDICTION RESULTS

CROSS-REFERENCE TO RELATED APPLICATION

The present application is a United States Bypass Continuation under 35 USC 111 (a) and claims the benefit of co-pending International Patent Application No. PCT/KR2021/014303 filed Oct. 15, 2021, which claims priority to Korean Patent Application 10-2020-0164903, filed Nov. 30, 2020, the entirety of each of which is hereby incorporated by reference.

TECHNICAL FIELD

The following description relates to technology regarding a method of segmenting a blood vessel image.

BACKGROUND ART

An interventional procedure to insert a stent using a catheter to treat cardiovascular, cerebrovascular, and peripheral blood vessels is widely spread. Before performing a procedure, the severity of a patient's lesion is evaluated through an angiography image. An angiography image is widely used to observe major blood vessels, diagnose a problem area in a blood vessel, and perform necessary procedures and measures. To quantitatively evaluate the severity of a lesion, it is required to know blood vessel information. Various methods of segmenting a blood vessel from an angiography image to obtain blood vessel information have been studied. Blood vessel segmenting information may be used in various ways in segmenting a centerline, measuring a branch angle, predicting a lesion location, and the like. Recently, a lot of methods of segmenting a blood vessel from an angiography image have been developed and have high accuracy compared to existing methods. When segmenting a blood vessel using a single model based on deep learning, accuracy is generally low and a lot of errors occur. Therefore, recently, an ensemble technique has been used for generating a blood vessel segmenting result by combining images generated using a plurality of blood vessel segmenting models.

DISCLOSURE OF THE INVENTION

Technical Solutions

A method, performed by a processor, of segmenting a blood vessel image according to an embodiment includes generating a plurality of candidate mask images regarding a target blood vessel by applying a plurality of blood vessel segmentation models to a blood vessel image, evaluating an error level for each of the generated plurality of candidate mask images, and generating a target blood vessel segmentation result from the candidate mask images based on the evaluated error level.

The evaluating of the error level for each of the generated plurality of candidate mask images may include, when at least one of pixels indicating a target blood vessel area in a corresponding candidate mask image is separated, evaluating the candidate mask image as an error.

The evaluating of the error level for each of the generated plurality of candidate mask images may include, when a number of pixels included in a blob other than a main blob in a corresponding candidate mask image is equal to or greater than a first threshold ratio compared to a number of pixels indicating a target blood vessel, evaluating the candidate mask image as an error.

The evaluating of the error level for each of the generated plurality of candidate mask images may include evaluating an error level of a corresponding candidate mask image based on a topology of an area indicating the target blood vessel in the corresponding candidate mask image.

The evaluating of the error level of the candidate mask image based on the topology of the area indicating the target blood vessel may include, based on a trend line calculated based on diameter information of the area indicating the target blood vessel in the candidate mask image, when there is an area having diameter information equal to or greater than a second threshold ratio from the trend line within the area indicating the target blood vessel, evaluating the candidate mask image as an error.

The evaluating of the error level of the candidate mask image based on the topology of the area indicating the target blood vessel may include, based on a trend line calculated based on brightness information of the area indicating the target blood vessel in the candidate mask image, when there is an area having a brightness difference equal to or greater than a third threshold ratio from the trend line within the area indicating the target blood vessel, evaluating the candidate mask image as an error.

The evaluating of the error level for each of the generated plurality of candidate mask images may include, when a length of a centerline of an area indicating a target blood vessel in a corresponding candidate mask image is equal to or less than a first threshold length, evaluating the candidate mask image as an error.

The generating of the target blood vessel segmentation result from the candidate mask images based on the evaluated error level may include generating a target blood vessel segmentation result based on candidate mask images obtained by excluding candidate mask images that are evaluated as errors from the plurality of candidate mask images.

The generating of the target blood vessel segmentation result from the candidate mask images based on the evaluated error level may include, when all of the plurality of candidate mask images are evaluated as errors, generating a target blood vessel segmentation result based on a candidate mask image having an error level equal to or less than a predetermined error level or a candidate mask image having a lowest error level.

The evaluating of the error level for each of the generated plurality of candidate mask images may include calculating an error score based on connectivity between pixels indicating a target blood vessel in a corresponding candidate mask image, calculating an error score based on a blob indicating the target blood vessel, calculating an error score based on a topology of an area indicating the target blood vessel, and calculating an error score based on a length of a centerline of the area indicating the target blood vessel.

An apparatus for segmenting a blood vessel image according to an embodiment includes an image receiver configured to receive a blood vessel image and a processor configured to generate a plurality of candidate mask images regarding a target blood vessel by applying a plurality of blood vessel segmentation models to the blood vessel image, evaluate an error level for each of the generated plurality of candidate mask images, and generate a target blood vessel segmentation result from the candidate mask images based on the evaluated error level.

Effects

When generating a blood vessel segmenting result from an existing angiography image using a plurality of blood vessel segmentation models, a blood vessel segmenting result may be derived by adding a predetermined weight to an individual blood vessel segmentation model. However, an existing blood vessel segmenting method does not perform an evaluation on an individual image that is generated using the individual blood vessel segmentation model. On the other hand, a blood vessel image segmenting apparatus according to an embodiment may individually perform an evaluation on a plurality of candidate mask images generated from an angiography image by applying a plurality of blood vessel segmentation model and may generate a blood vessel segmentation result based on an individually evaluated candidate mask image. A blood vessel image segmenting apparatus according to an embodiment may generate a blood vessel segmentation result by excluding a candidate mask image obviously determined to be an error and thus may generate a more accurate blood vessel segmentation result compared to an existing method. Furthermore, a blood vessel image segmenting apparatus according to an embodiment may generate and present to a user a blood vessel segmentation result based on only a plurality candidate mask images generated by applying a plurality of blood vessel segmentation models, without any blood vessel information (for example, blood vessel curvature information, brightness information, branch information, and the like).

BEST MODE FOR CARRYING OUT THE INVENTION

Figure 1:
FIG. 1 illustrates an angiography image.

The following structural or functional descriptions of embodiments are merely intended for the purpose of describing the embodiments and the embodiments may be implemented in various forms. The embodiments are not meant to be limited, but it is intended that various modifications, equivalents, and alternatives are also covered within the scope of the claims.

Although terms of "first" or "second" are used to explain various components, the components are not limited to the terms. These terms should be used only to distinguish one component from another component. For example, a "first" component may be referred to as a "second" component, and similarly, the "second" component may be referred to as the "first" component within the scope of the right according to the concept of the present disclosure.

It will be understood that when a component is referred to as being "connected to" another component, the component can be directly connected or coupled to the other component or intervening components may be present.

As used herein, the singular forms "a," "an," and "the" are intended to include the plural forms as well, unless the context clearly indicates otherwise. As used herein, the terms "include," "comprise," and "have" specify the presence of stated features, numbers, operations, elements, components, and/or combinations thereof, but do not preclude the presence or addition of one or more other features, numbers, operations, elements, components, and/or combinations thereof.

Unless otherwise defined, all terms used herein including technical or scientific terms have the same meanings as those generally understood by one of ordinary skill in the art. Terms, such as those defined in commonly used dictionaries, should be construed to have meanings matching with contextual meanings in the relevant art and the present disclosure, and are not to be construed as an ideal or excessively formal meaning unless otherwise defined herein.

Hereinafter, embodiments will be described in detail with reference to the accompanying drawings. When describing the embodiments with reference to the accompanying drawings, like reference numerals refer to like components and a repeated description related thereto will be omitted.

FIG. 1 illustrates an angiography image according to an embodiment.

An angiography image is used to observe a blood vessel, diagnose a problem area in a blood vessel, and perform necessary procedures and measures. To quantitatively evaluate the type and degree of a lesion, it is required to know blood vessel information. A method of segmenting a blood vessel from an angiography image to obtain blood vessel information has been studied. According to an embodiment, an image receiver of a blood vessel image segmenting apparatus may receive an angiography image 100 captured by a blood vessel image capturing apparatus. An angiography image is an image capturing a blood vessel of a living body and may be generated using a coronary angiography (CAG) image and/or a magnetic resonance imaging (MRI) image. For example, a blood vessel image may be an image obtained by taking an X-ray of a living body injected with a contrast medium.

A blood vessel image segmenting apparatus according to an embodiment may segment a blood vessel from an angiography image using a plurality of blood vessel segmentation models based on deep learning. Hereinafter, a method of segmenting a blood vessel from an angiography image is described in detail.

Figure 2:
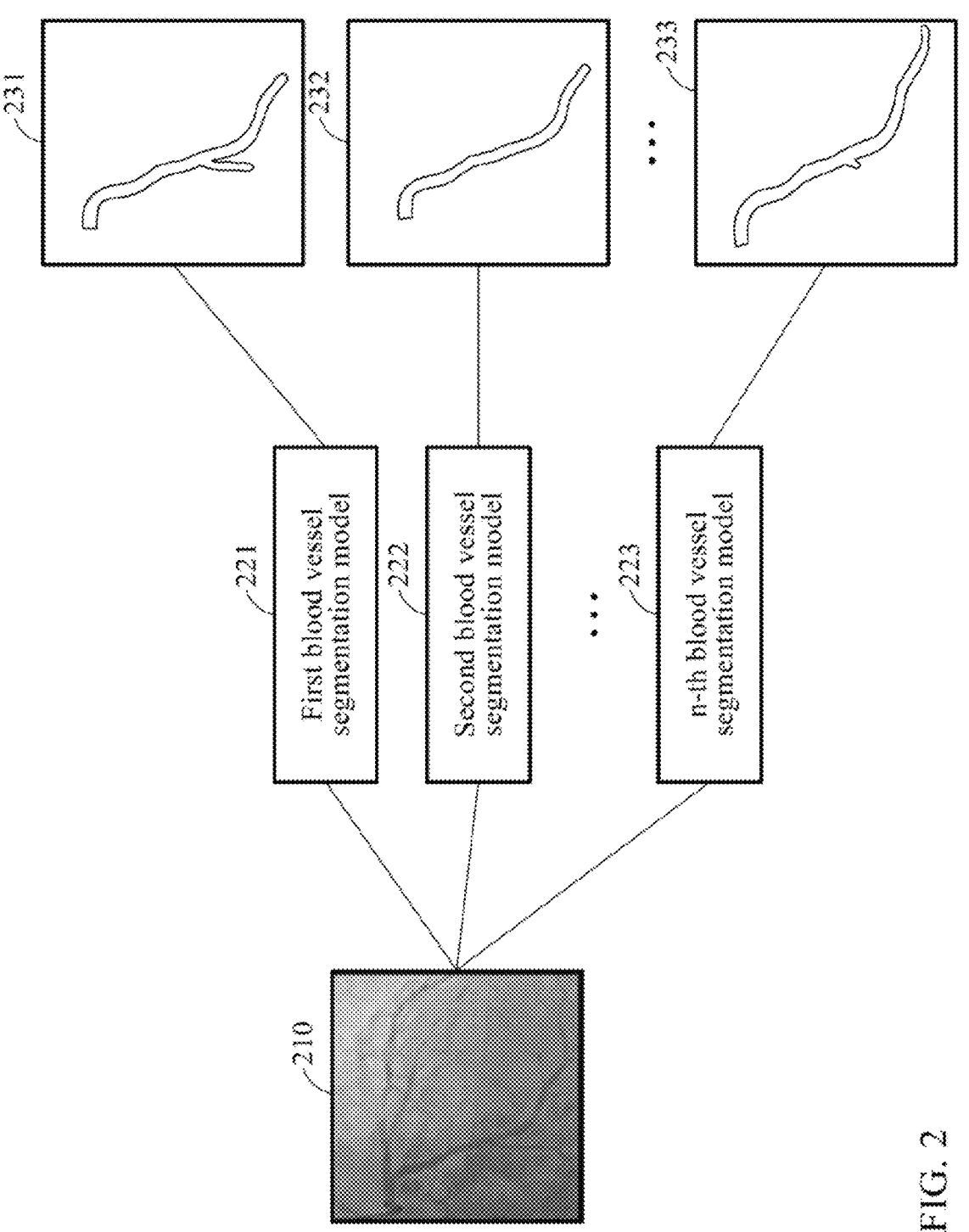
FIG. 2 illustrates a process of generating candidate mask images regarding a target blood vessel by applying a plurality of blood vessel segmentation models to an angiography image.

FIG. 2 illustrates a process of segmenting candidate mask images regarding a target blood vessel by applying a plurality of blood vessel segmentation models to a blood vessel image.

A blood vessel image segmenting apparatus may segment a target blood vessel from an angiography image 210 that the blood vessel image segmenting apparatus received. A target blood vessel may indicate a blood vessel that a blood vessel image segmenting apparatus is to segment from an angiography image. A blood vessel image segmenting apparatus may segment a target blood vessel from a blood vessel image based on at least one machine learning model. A machine learning model may be at least one model having a machine learning structure designed to segment a target blood vessel from a blood vessel image in response to an input of a blood vessel image and may include, for example, a neural network. A blood vessel image segmenting apparatus may calculate an segmentation result of a target blood vessel by performing an operation on a received blood vessel image according to the above machine learning model. For example, output data of a machine learning model may include a score corresponding to the likelihood (for example, probability) of each pixel in a plurality of pixels in a blood vessel image indicating a target blood vessel. A blood vessel image segmenting apparatus may generate an segmentation result of a target blood vessel by determining a pixel in output data that has a score equal to or greater than a threshold value as a target blood vessel. In another example, output data of a machine learning model may be a target blood vessel area segmented from a blood vessel image and may include a pixel selected from a plurality of pixels of the blood vessel image as a target blood vessel. An segmentation result of a target blood vessel may be, for example, a set of pixels selected from pixels of a blood vessel image as target blood vessels and/or an image (e.g., a target blood vessel image) corresponding to a target blood vessel area segmented from a blood vessel image.

For reference, a neural network may include a deep neural network (DNN). ADNN may include a fully connected network, a deep convolutional network, a recurrent neural network, and the like. A neural network may perform object classification, object recognition, radar image recognition, and the like by mapping input data and output data in a non-linear relationship to each other, based on deep learning. Deep learning is a machine-learning technique to solve a problem such as object recognition from a big data set and may map input data and output data to each other through supervised or unsupervised learning. In supervised learning, the machine learning model may be trained based on training data including a set of a training input (for example, a blood vessel image for training) and a training output (for example, a ground truth image segmented as a target blood vessel by an expert or the like, with respect to the blood vessel image for training) mapped to a corresponding input. For example, a machine learning model may be trained to output a training output from a training input. A machine learning model during training (hereinafter, referred to as "a temporary model") may generate a temporary output in response to a training input and may be trained so that a loss between the temporary output and the training output (for example, ground truth) is minimized. During a training process, a parameter (for example, a connection weight between nodes/layers in a neural network) of a machine learning model may be updated according to a loss.

As described above, a blood vessel image segmenting apparatus may store a plurality of machine learning models. A blood vessel image segmenting apparatus may selectively use a machine learning model to be used in segmenting a target blood vessel according to a user's input, among a plurality of machine learning models. For example, a blood vessel image segmenting apparatus may store a plurality of machine learning models for each type of blood vessel (for example, left main coronary artery (LM), left anterior descending artery (LAD), left circumflex artery (LCX), and right coronary artery (RCA)) and/or for each area of blood vessels (for example, a proximal area (proximal region), a middle area (mid region), and a distal area (distal region)). For reference, a blood vessel area may be classified into a proximal point (proximal portion), a middle point (middle portion), and a distal area (distal portion) according to a distance from a blood vessel point in which a catheter is inserted but may not be limited thereto. A blood vessel area may be classified according to a ratio of the distance from a point on a blood vessel insertion part in which a contrast medium may be injected to obtain a blood vessel image to the distance from a blood vessel terminal in which a contrast medium may be inserted.

In addition, a blood vessel image segmenting apparatus may store a plurality of machine learning models for each area and type of blood vessel. For example, a blood vessel image segmenting apparatus may store a plurality of machine learning models for segmenting an LM as a target blood vessel. The type of target blood vessel segmentated by a blood vessel image segmenting apparatus may vary depending on a user's input. A blood vessel image segmenting apparatus may receive a user's input from a user, which may include information of the area and/or type of target blood vessel to be segmented. A blood vessel image segmenting apparatus may receive a user's input, select the area and/or type of blood vessel to be segmented, and load at least one machine learning model corresponding to the selected area and/or type of blood vessel. For example, when a blood vessel image segmenting apparatus receives a user's input and segments a main blood vessel as a target blood vessel, the blood vessel image segmenting apparatus may load at least one machine learning model corresponding to the main blood vessel. In other words, a blood vessel image segmenting apparatus may load at least one machine learning model corresponding to the area and/or type of blood vessel determined according to a user's input. A blood vessel image segmenting apparatus may generate segmentation results of a target blood vessel corresponding to a selected area and/or type of blood vessel from a blood vessel image, using at least one loaded machine learning model. Each of machine learning models stored in the blood vessel image segmenting apparatus may be respectively trained based on training data corresponding to the area and/or type of blood vessel. A trained parameter of machine learning models may be different for each area and/or type of blood vessel, and a machine learning structure (for example, a convolutional neural network (CNN), a U-Net architecture, and the like) may be different from one another. A plurality of machine learning models having the same area and/or type of blood vessel may have different trained parameters and different machine learning structures. Thus, a blood vessel image segmenting apparatus may load one or more machine learning models corresponding to the area and/or type of blood vessel selected according to a user's input, and the one or more machine learning models may have the same area and/or type of target blood vessel but segment target blood vessels different from each other. Hereinafter, a machine learning model that a blood vessel image segmenting apparatus may apply to segment a target blood vessel is referred to as a blood segmentation model.

A blood vessel image segmenting apparatus according to an embodiment may generate a target blood vessel segmentation result from a blood vessel image by applying a plurality of blood vessel segmentation models.

First, a blood vessel image segmenting apparatus may generate a plurality of candidate mask images regarding a target blood vessel by applying a plurality of blood vessel segmentation models to a blood vessel image. An image receiver of a blood vessel image segmenting apparatus may receive the angiography image 210 captured by a blood vessel image capturing apparatus. A blood vessel image segmenting apparatus may receive a user's input, select the area and/or type of a target blood vessel to be segmented, and load a plurality of blood vessel segmentation models (e.g., a first blood vessel segmentation model 211, a second blood vessel segmentation model 222, and an n-th blood vessel segmentation model 223) corresponding to the selected area and/or type of blood vessel. A blood vessel image segmenting apparatus may segment the first to n-th candidate mask images 231 to 233 regarding a target blood vessel by applying the loaded plurality of blood vessel segmentation models to the angiography image 210. For example, the first candidate mask image 231 may be generated by applying the loaded first blood vessel segmentation model 221 to the angiography image 210 and the second candidate mask image 232 may be generated by applying the loaded second blood vessel segmentation model 222 to the angiography image 210. The plurality of blood vessel segmentation models (the first to n-th blood vessel segmentation models 221 to 223) may have the same area and/or type of target blood vessel to be segmented from the angiography image 210 but may generate different candidate mask images, regarding the target blood vessel, since the trained parameter and machine learning structure of the machine learning models are different from each other.

Figure 3:
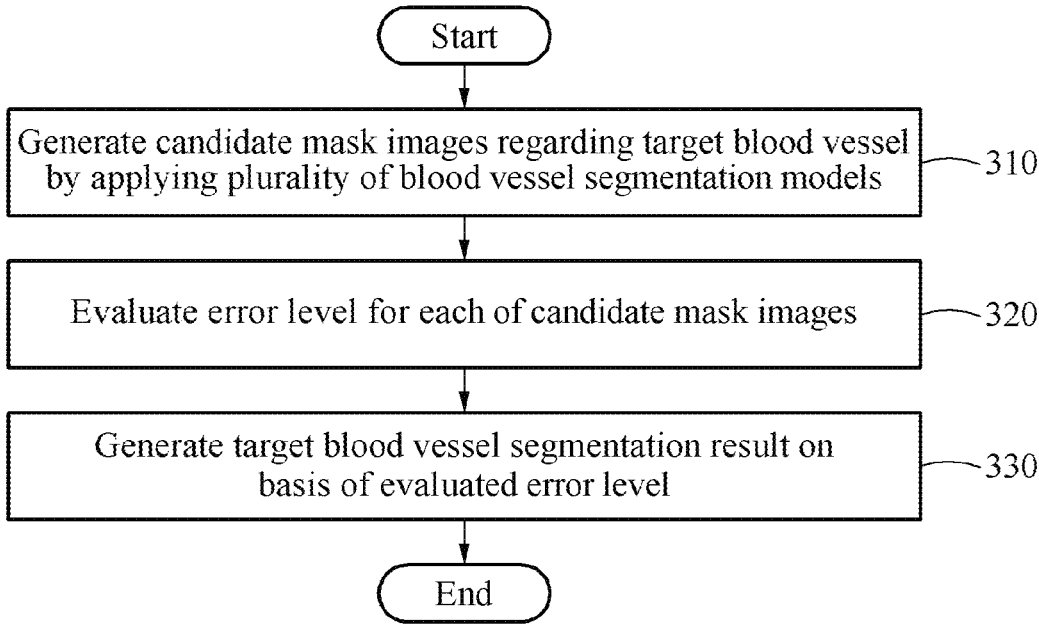
FIG. 3 is a flowchart illustrating a method of generating a target blood vessel segmentation result, according to an embodiment.

FIG. 3 is a flowchart illustrating a method of generating a target blood vessel segmentation result, according to an embodiment.

First, a blood vessel image segmenting apparatus may select, according to a user's input, the area and type of target blood vessel from which an segmentation result is generated and may load a plurality of blood vessel segmentation models to be used for segmenting the corresponding target blood vessel. In operation 310, a blood vessel image segmenting apparatus may generate candidate mask images regarding a target blood vessel, for each blood vessel segmentation model, by applying the loaded plurality of blood vessel segmentation models to a blood vessel image received by an image receiver. In operation 320, a blood vessel image segmenting apparatus may evaluate an error level of each of the generated candidate mask images. In operation 330, a target blood vessel segmentation result may be generated based on the evaluated error level of each of the candidate mask images.

Figure 4:
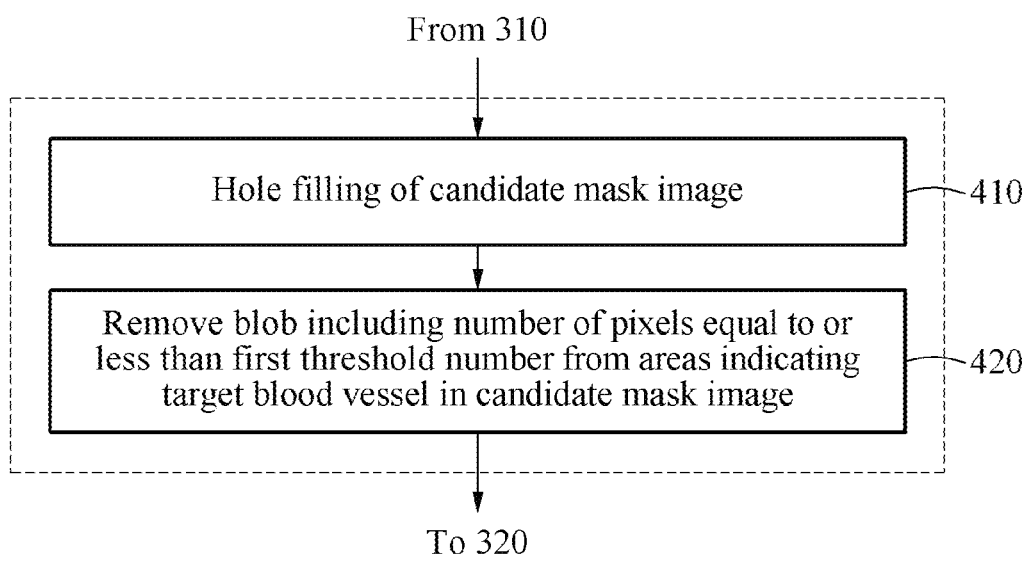
FIG. 4 illustrates a process of post-processing candidate mask images generated by applying a plurality of blood vessel segmentation models.

FIG. 4 describes a process of post-processing candidate mask images generated by applying a plurality of blood vessel segmentation models.

A blood vessel image segmenting apparatus may generate candidate mask images regarding a target blood vessel by applying a plurality of blood vessel segmentation models and may subsequently perform post-processing on the candidate mask images. In other words, a blood vessel image segmenting apparatus may perform post-processing on the generated candidate mask images and subsequently evaluate an error level for the post-processed plurality of candidate mask images.

Specifically, in operation 410 during a post-processing process, a hole may be filled in each of the candidate mask images. Hole filling may refer to filling a hole in a candidate mask image using a neighboring pixel. For example, when a candidate mask image regarding a target blood vessel is generated from an angiography image by applying a blood vessel segmentation model, holes may occur due to detection failure of some pixels in the generated candidate mask image. It may be possible that, for some pixels in the candidate mask image, information to fill a corresponding pixel area is missing and that the corresponding pixel area remains as a hole. When there is a hole in the candidate mask image, a blood vessel image segmenting apparatus may fill the hole in the image using a neighboring pixel. For example, when there is a hole in an area indicating a target blood vessel in the generated candidate mask image, a blood vessel image segmenting apparatus may change pixel information so that a plurality of pixels corresponding to the hole may indicate the target blood vessel.

Subsequently, in operation 420 during the post-processing process, blobs including pixels in a number equal to or less than a first threshold value may be removed from areas indicating a target blood vessel, for each of the candidate mask images. In the present specification, a blob may refer to an area in which pixels having similar information are connected to each other and may indicate an area in which pixels indicating a target blood vessel are connected to each other. A blood vessel image segmenting apparatus may perform post-processing so that only blobs including pixels in a number greater than a first threshold value may indicate a target blood vessel in a candidate mask image by removing blobs including pixels in a number equal to or less than the first threshold value from areas indicating the target blood vessel. A first threshold value may be adjusted according to a user's input.

To sum up, a blood vessel image segmenting apparatus may generate candidate mask images regarding a target blood vessel for each blood vessel segmentation model, and after post-processing each of the generated candidate mask images through operation 410 and operation 420, may evaluate an error level for each of the candidate mask images. Hereinafter, a process of evaluating an error level of a candidate mask image is described.

Figure 5:
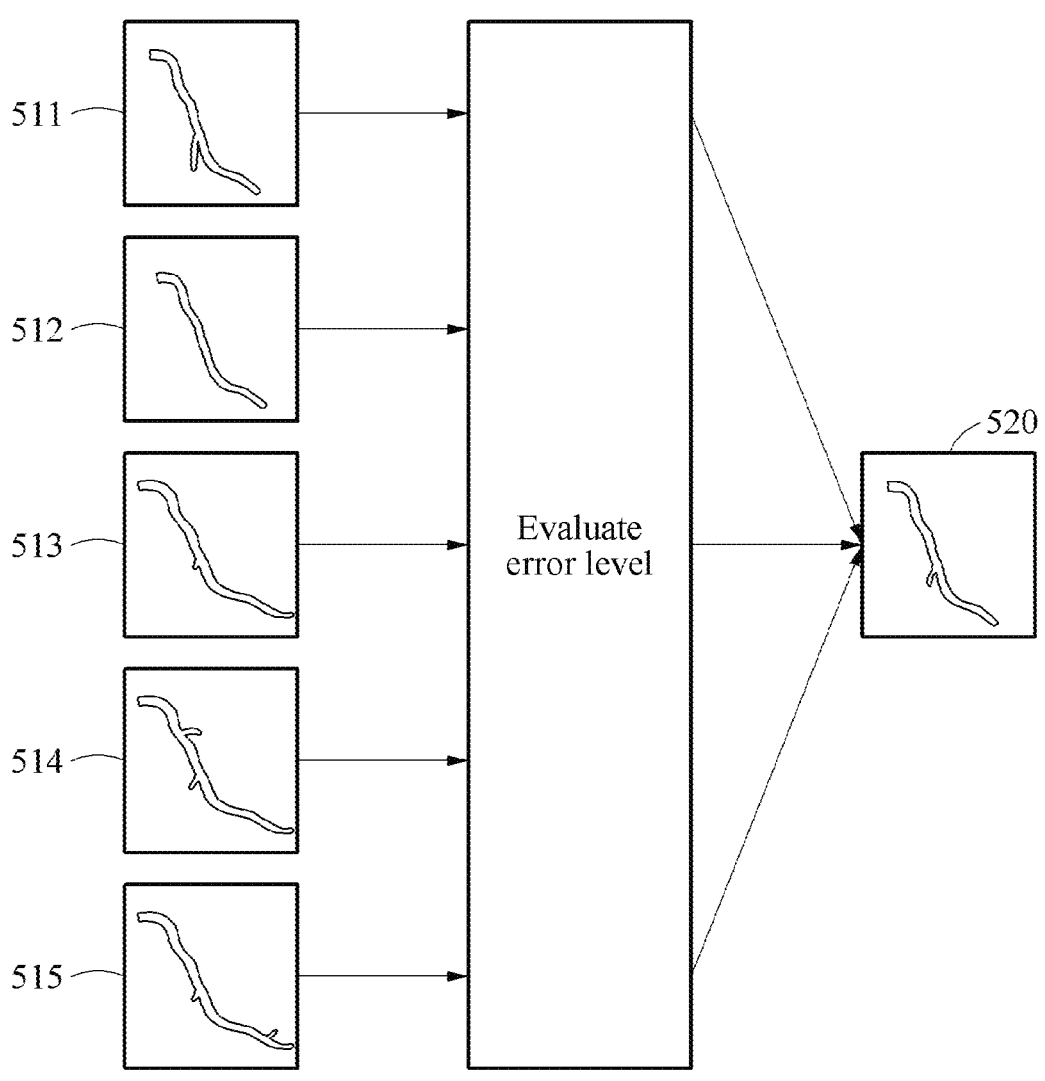
FIG. 5 illustrates a process of generating a target blood vessel segmentation result by evaluating error levels of candidate mask images according to an embodiment.

FIG. 5 illustrates a process of generating a target blood vessel segmentation result by evaluating error levels of candidate mask images according to an embodiment.

A blood vessel image segmenting apparatus may generate candidate mask images 511 to 515 regarding a target blood vessel, for each blood vessel segmentation model, by applying a loaded plurality of blood vessel segmentation models to a blood vessel image. A blood vessel image segmenting apparatus may perform post-processing on each of the generated candidate mask images and subsequently evaluate an error level for each of the candidate mask images. A blood vessel image segmenting apparatus may evaluate an error level of each of the candidate mask images based on connectivity of pixels indicating a target blood vessel area. In addition, a blood vessel image segmenting apparatus may also evaluate an error level of each of the candidate mask images based on a blob, the topology of an area indicating a target blood vessel, or the length of a centerline of an area indicating a target blood vessel. A centerline may refer to a line passing through the center of an area indicating a target blood vessel in a candidate mask image.

A blood vessel image segmenting apparatus may evaluate an error level for each of the generated candidate mask images 511 to 515 and subsequently generate a target blood vessel segmentation result 520 from the candidate mask images 511 to 515 based on the evaluated error level. According to an embodiment, a blood vessel image segmenting apparatus may generate a target blood vessel segmentation result using only some of the candidate mask images, for example, the candidate mask images 511, 513, and 515. For example, a blood vessel image segmenting apparatus may use a candidate mask image having the highest evaluation among candidate mask images as a target blood vessel segmentation result. In another example, a blood vessel image segmenting apparatus may generate a target blood vessel segmentation result by combining remaining candidate mask images after excluding candidate mask images that are evaluated as an error among candidate mask images.

Figure 6:
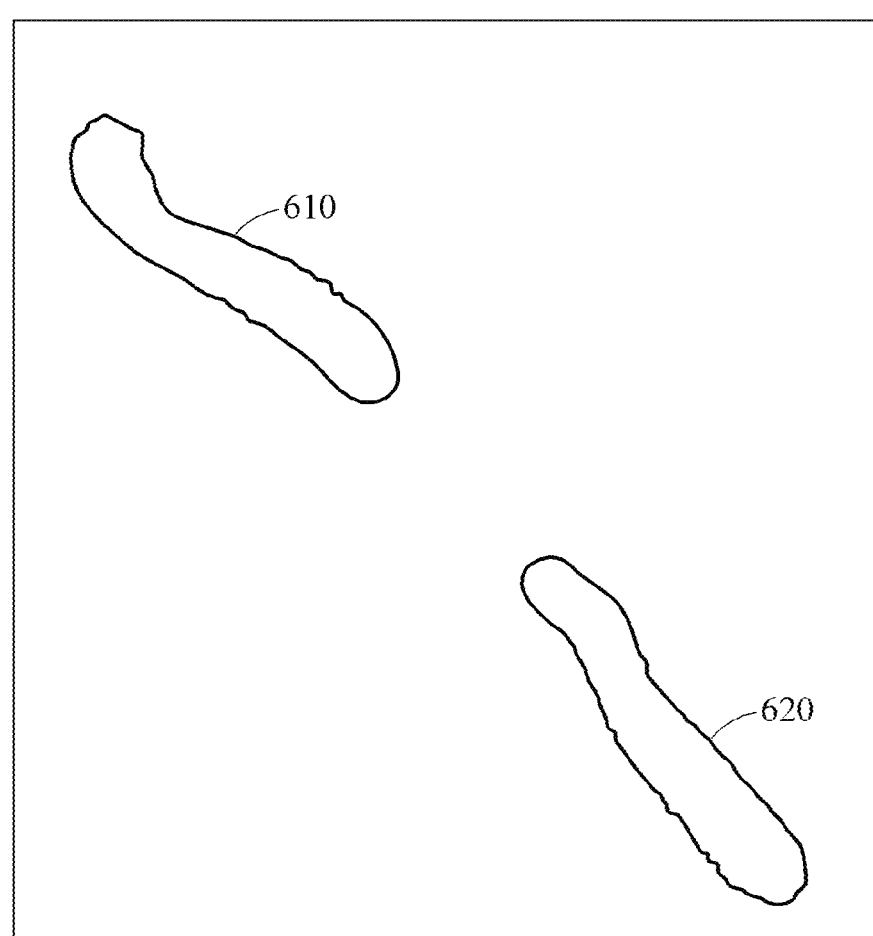
FIG. 6 illustrates a process of evaluating an error level of a candidate mask image based on connectivity of pixels indicating a target blood vessel area.

FIG. 6 illustrates a process of evaluating an error level of a candidate mask image based on connectivity of pixels indicating a target blood vessel area.

A blood vessel image segmenting apparatus may evaluate an error level based on connectivity of pixels indicating a target blood vessel area, for each generated candidate mask image. When at least one of pixels indicating a target blood vessel area in a candidate mask image 600 is separated, a blood vessel image segmenting apparatus May evaluate the corresponding candidate mask image 600 as an error.

According to an embodiment, a blood vessel image segmenting apparatus may determine whether each of pixels included in the candidate mask image 600 corresponds to a pixel indicating a target blood vessel. For example, the blood vessel image segmenting apparatus may give a pixel value to each of the pixels included in the candidate mask image 600. In the candidate mask image 600, a pixel value of each pixel may represent whether a corresponding pixel position indicates a target blood vessel. For example, the blood vessel image segmenting apparatus may compare a pixel value given to each pixel in the candidate mask image 600 to a threshold value. When the pixel value exceeds the threshold value, the corresponding pixel may be determined as a pixel indicating a target blood vessel, and when the pixel value is equal to or less than the threshold value, the corresponding pixel may be determined as a pixel not indicating a target blood vessel.

Since a blood vessel image segmenting apparatus may be in a state in which blobs having a size equal to or less than a first threshold value are previously removed from a candidate mask image generateed from a blood vessel segmentation model through a post-processing process, and since a target blood vessel may generally be connected rather than separated, pixels indicating a target blood vessel in a candidate mask image after post-processing may generally be connected to each other. Thus, when at least one of pixels indicating a target blood vessel area in the candidate mask image 600 is separated, a blood vessel image segmenting apparatus may evaluate the corresponding candidate mask image as an error. For example, the candidate mask image 600 may include a first blob 610 and a second blob 620, in which pixels indicating a target blood vessel are connected to each other. A blood vessel image segmenting apparatus may evaluate the candidate mask image 600 as an error based on the first blob 610 and the second blob 620 that are separatee from each other. In other words, since pixels included in the first blob 610 and pixels included in the second blob 620 in the candidate mask image 600 are separated from each other, a blood vessel image segmenting apparatus may evaluate the corresponding candidate mask image 600 as an error.

Figure 7:
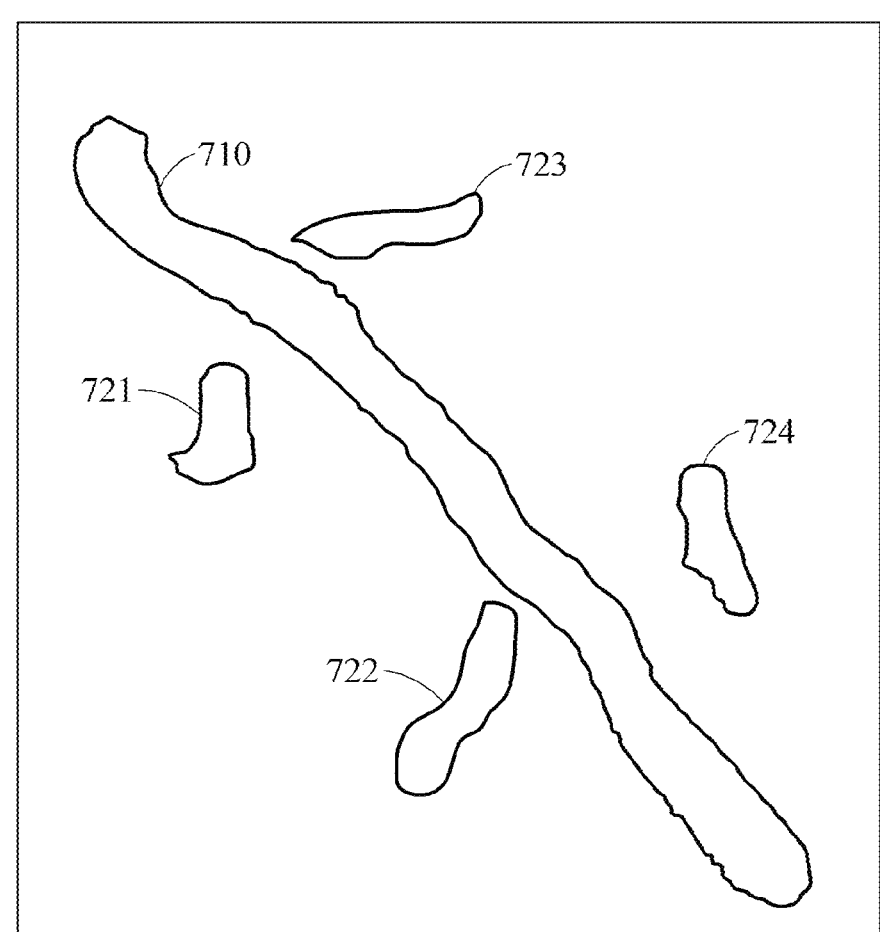
FIG. 7 illustrates a process of evaluating an error level of a candidate mask image based on a blob indicating a target blood vessel.

FIG. 7 illustrates a process of evaluating an error level of a candidate mask image based on a blob indicating a target blood vessel.

A blood vessel image segmenting apparatus may evaluate an error level for an individual candidate mask image based on blobs indicating a target blood vessel. A blood vessel image segmenting apparatus may detect one or more blobs, which appear as a pixel cluster in which pixels indicating a target blood vessel are connected to each other in a candidate mask image 700. Since a target blood vessel may generally be composed of long, connected blood branches connected to each other, a blood vessel image segmenting apparatus may determine a blob 710 including the largest number of pixels among one or more blobs detected in the candidate mask image 700 as a blob closest to a target blood vessel desired by a user for segmentation. Hereinafter, a blob having the largest number of pixels among blobs detected regarding the candidate mask image 700 is referred to as a main blob. A blood vessel image segmenting apparatus may determine other blobs 721, 722, 723, and 724 other than a main blob 710 in a candidate mask image 700 as areas having little relevance to Ha target blood vessel. When a lot of the other blobs 721 to 724 other than the main blob 710 are detected regarding the candidate mask image 700, a blood vessel image segmenting apparatus may evaluate the corresponding candidate mask image 700 as an error. Specifically, when the number of pixels included in the blobs 721 to 724 other than the main blob 710 is equal to or greater than a first threshold ratio compared to the number of pixels indicating a target blood vessel in the candidate mask image 700, the blood vessel image segmenting apparatus may evaluate the corresponding candidate mask image 700 as an error. For example, the first threshold ratio may represent 5% but is not limited thereto.

FIGS. 8A to 10 describe a process of evaluating an error level regarding a candidate mask image based on the topology of an area indicating a target blood vessel.

A blood vessel image segmenting apparatus may, regarding a candidate mask image generated by applying a blood vessel segmentation model, evaluate an error level of the candidate mask image based on the topology of an area indicating a target blood vessel. The topology of an area indicating a target blood vessel may mean diameter information, brightness information, curvature information, and structure data of the area indicating a target blood vessel. Specifically, a blood vessel image segmenting apparatus may evaluate an error level based on the topology of a main blob among a plurality of blobs indicating a target blood vessel regarding a candidate mask image.

Figure 8A:
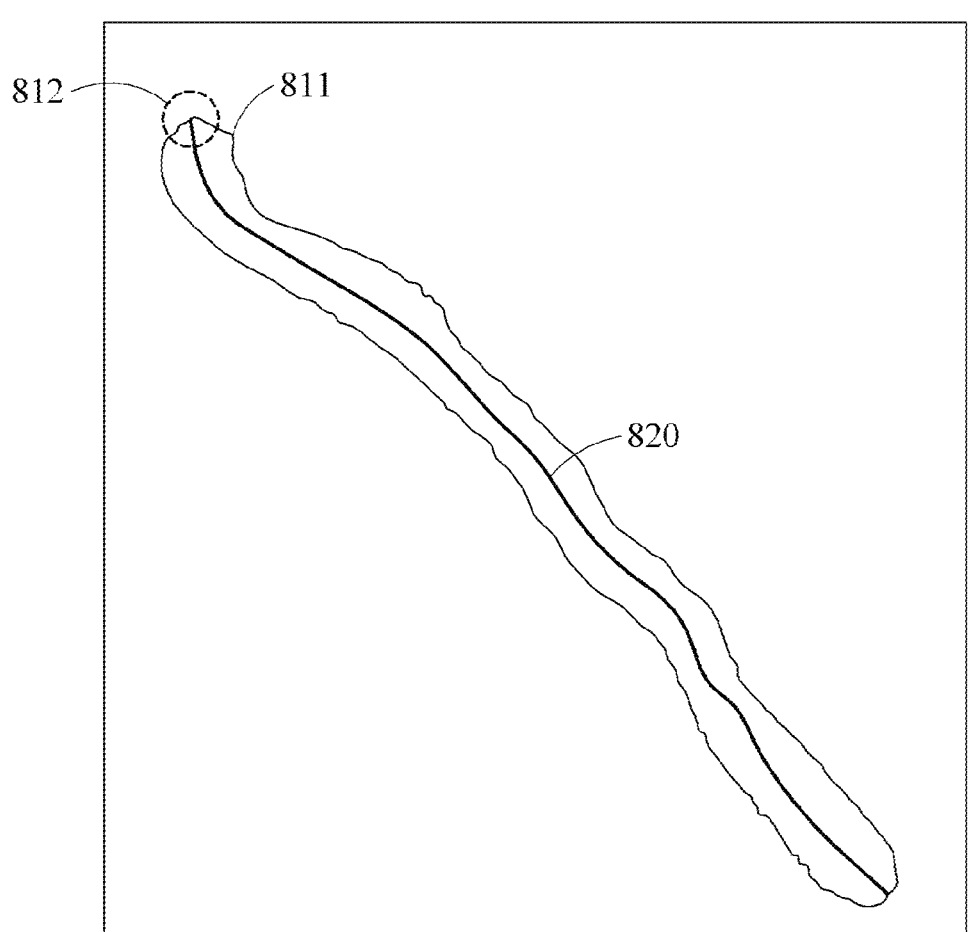
FIG. 8A illustrates a main blob detected from a candidate mask image.

FIG. 8A illustrates a main blob detected from a candidate mask image.

According to an embodiment, a blood vessel image segmenting apparatus may detect a main blob 811 in a candidate mask image 800. A blood vessel image segmenting apparatus may determine a line passing through the center of an area corresponding to the detected main blob 811 as a centerline 820 of the candidate mask image 800. In addition, a blood vessel image segmenting apparatus may determine a start point 812 of the detected main blob 811 as the start point of a target blood vessel. Hereinafter, a specific process of evaluating an error level based on the topology of an area indicating a target blood vessel is described.

Figure 8B:
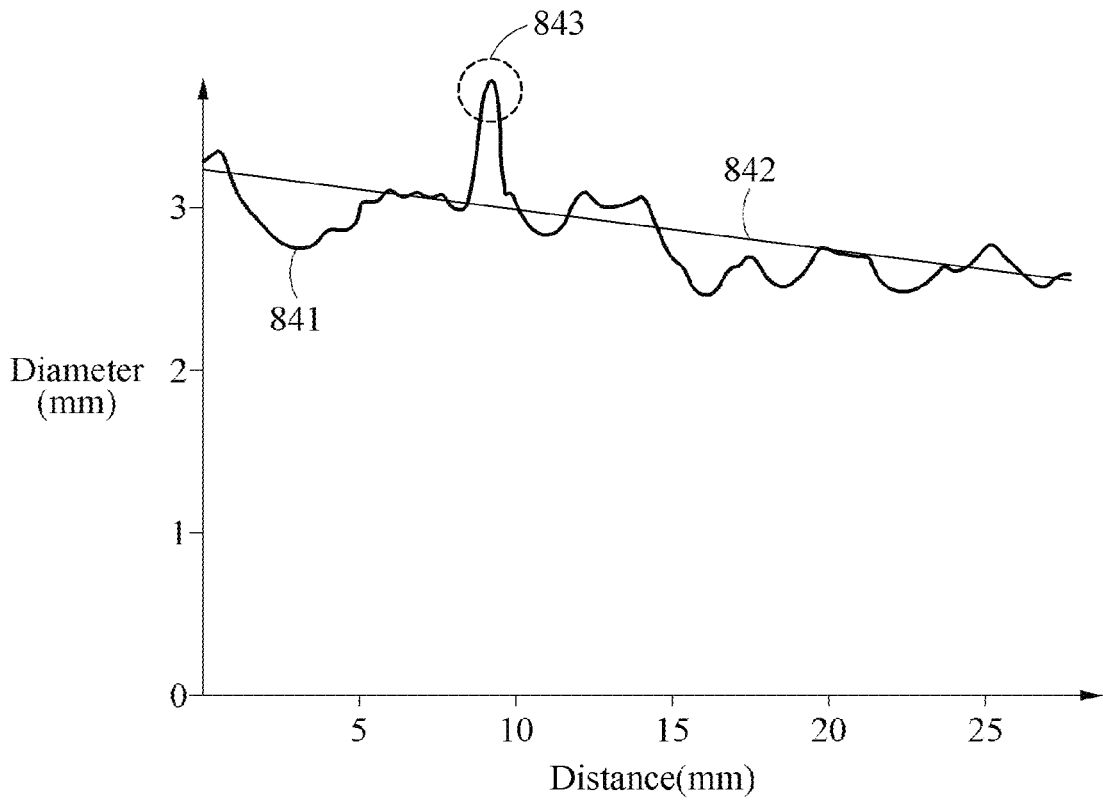
FIG. 8B illustrates a graph of diameter size according to the distance from the start point of a main blob.

FIG. 8B illustrates a graph of diameter size according to the distance from the start point of a main blob.

A blood vessel image segmenting apparatus may evaluate an error level based on diameter information of an area indicating a target blood vessel regarding the candidate mask image 800. First, the blood vessel image segmenting apparatus may determine the start point 812 of the main blob 811, which is considered as the start point of a target blood vessel in the main blob 811, regarding the corresponding candidate mask image 800. The blood vessel image segmenting apparatus may determine the size of the diameter of a blood vessel area corresponding to the distance from the start point 812 of the main blob 811 along the centerline 820. A graph 841 may represent the size of the blood vessel diameter according to the distance from the start point 812 of the main blob 811 along the centerline 820. The blood vessel image segmenting apparatus may calculate a trend line 842 using the size of the diameter of a blood vessel in the main blob 811 detected in the candidate mask image 800.

The blood vessel image segmenting apparatus may calculate the trend line 842 for the diameter size of an area indicating a target blood vessel using the size of the blood vessel diameter of the main blob 811 regarding the candidate mask image 800. Since the diameter of a blood vessel generally narrows along the distal end of the blood vessel, a portion of a blood vessel having a larger diameter above a trend line for the diameter of an area indicating a target blood vessel may be an area incorrectly detected as a target blood vessel. Thus, based on a trend line calculated based on the diameter size of an area indicating a target blood vessel, when there is an area 843 having a difference in diameter equal to or greater than a second threshold ratio from the trend line 842 in the area indicating the target blood vessel, the blood vessel image segmenting apparatus may determine the candidate mask image 800 as an error. For example, a second threshold ratio may represent 20% but is not limited thereto.

Furthermore, when a lesion area is detected from a received angiography image, the blood vessel image segmenting apparatus may also calculate a trend line based on the diameter size of an area excluding the lesion area from an area indicating a target blood vessel regarding the candidate mask image 800. For example, when the blood vessel image segmenting apparatus detects a lesion area considered as cancer, the blood vessel image segmenting apparatus may calculate a trend line for the diameter size of an area excluding the lesion area considered as cancer from an area indicating a target blood vessel. Based on a trend line calculated excluding a lesion area, when there is an area having a difference in diameter equal to or greater than a second threshold ratio from the trend line in an area indicating a target blood vessel, the blood vessel image segmenting apparatus may determine a candidate mask image as an error.

Figure 8C:
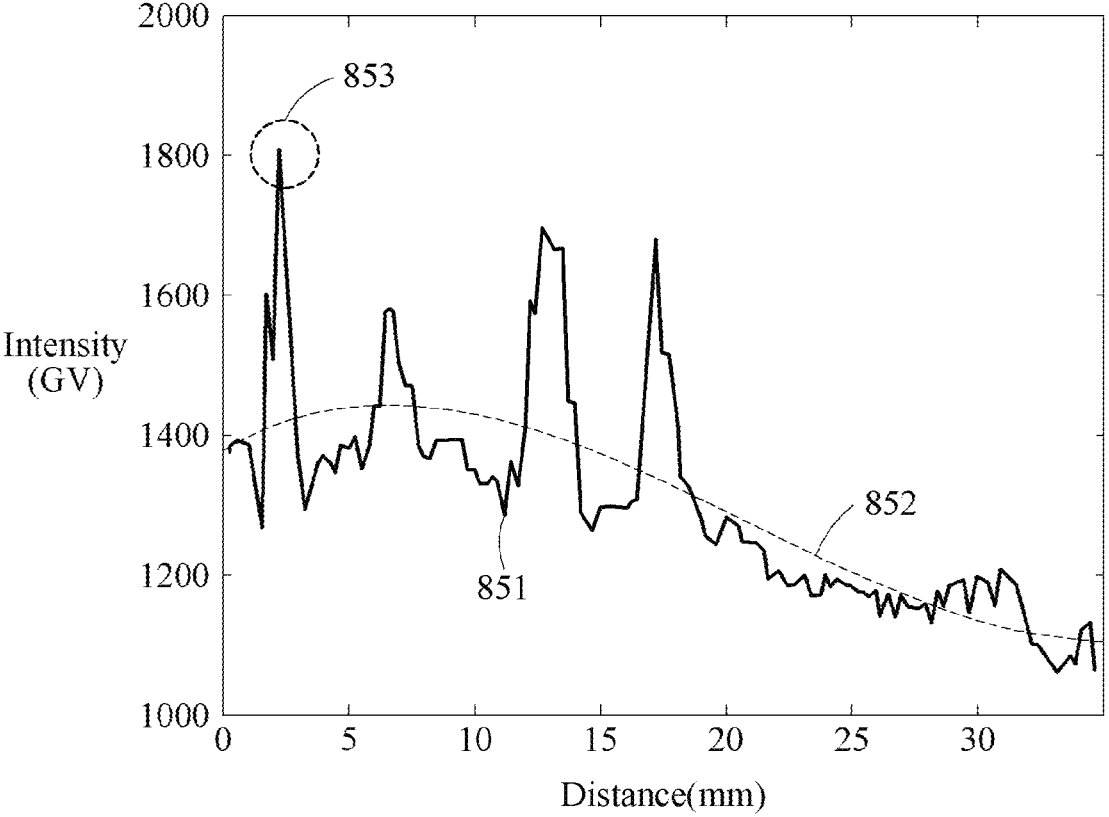
FIG. 8C illustrates a graph of brightness intensity according to the distance from the start point of a main blob.

FIG. 8C illustrates a graph of brightness intensity according to the distance from the start point of a main blob.

A blood vessel image segmenting apparatus may evaluate an error level based on the brightness intensity of an area indicating a target blood vessel regarding the candidate mask image 800. For example, a brightness intensity may represent distribution concentration of a contrast medium injected to obtain a blood vessel image. First, a blood vessel image segmenting apparatus may determine the start point 812 of the main blob 811, which is considered as the start point of a target blood vessel in the main blob 811, regarding the corresponding candidate mask image 800. A blood vessel image segmenting apparatus may determine brightness intensity of a blood vessel area corresponding to the distance from the start point 812 of the main blob 811 along the centerline 820. A graph 851 may represent blood vessel brightness intensity according to the distance from the start point 812 of the main blob 811 along the centerline 820. A blood vessel image segmenting apparatus may calculate a trend line 852 using blood vessel brightness intensity in the main blob 811 detected in the candidate mask image 800. A blood vessel image segmenting apparatus may calculate the trend line 852 for brightness intensity of an area indicating a target blood vessel using blood vessel brightness intensity of the main blob 811 regarding the candidate mask image 800. Since distribution of a contrast medium may generally not be significantly different between adjacent blood vessels, a change in brightness intensity of pixels indicating an adjacent blood vessel may have to be not big. A blood vessel image segmenting apparatus may, according to a change in brightness intensity of an area indicating a target blood vessel in the candidate mask image 800, evaluate an error regarding a corresponding candidate mask image. Specifically, based on the trend line 852 calculated based on brightness intensity of an area indicating a target blood vessel in the candidate mask image 800, when there is an area 853 having a difference in brightness intensity equal to or greater than a third threshold ratio from the trend line 852 in the area indicating the target blood vessel, a blood vessel image segmenting apparatus may determine the corresponding candidate mask image 800 as an error. For example, a third threshold ratio may represent 30% but is not limited thereto.

In addition, the blood vessel image segmenting apparatus may also evaluate an error level using structure data or curvature information of an area indicating a target blood vessel regarding a candidate mask image.

According to an embodiment, a blood vessel image segmenting apparatus may evaluate an error level of a candidate mask image using structure data of an area indicating a target blood vessel. For example, a blood vessel image segmenting apparatus may receive a user's input and segment a main blood vessel as a target blood vessel. A main blood vessel may represent one important blood vessel in a blood vessel area and may generally not have a y-shaped branch area. Thus, when a y-shaped branch area is detected in an area indicating a main blood vessel in a candidate mask image, a blood vessel image segmenting apparatus may evaluate the corresponding candidate mask image as an error. The embodiment described above may only be an example of when a target blood vessel is a main blood vessel. A blood vessel image segmenting apparatus may evaluate an error level of a candidate mask image by evaluating structure data of an area indicating a target blood vessel in a candidate mask image using different methods according to the type of target blood vessel received from a user.

According to an embodiment, a blood vessel image segmenting apparatus may also evaluate an error level using curvature information of an area indicating a target blood vessel. For example, when there is a branch area in an area indicating a target blood vessel in a candidate mask image, a blood vessel image segmenting apparatus may evaluate the corresponding candidate mask image as an error in response to a curvature between adjacent branch areas exceeding a threshold curvature.

Figure 9:
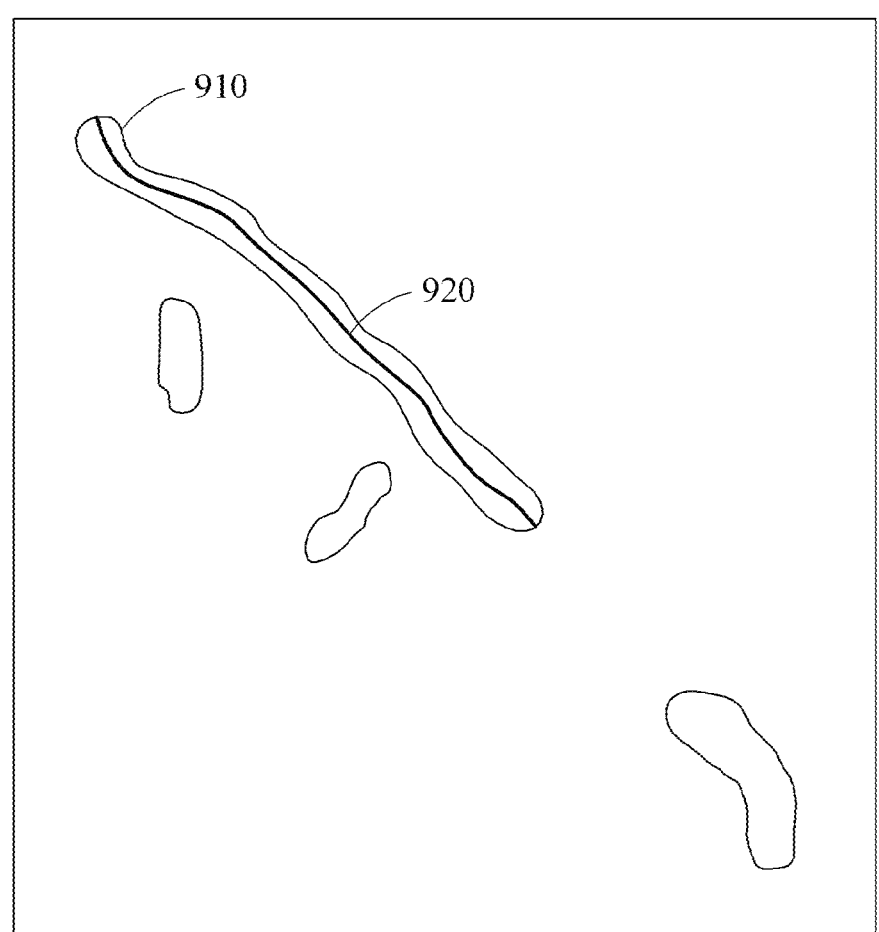
FIG. 9 illustrates a process of evaluating an error level of a candidate mask image based on the length of a centerline of an area indicating a target blood vessel.

FIG. 9 illustrates a process of evaluating an error level of a candidate mask image based on the length of a centerline of an area indicating a target blood vessel.

A blood vessel image segmenting apparatus may evaluate an error level based on the length of a centerline of an area indicating a target blood vessel regarding a candidate mask image 900. A blood vessel image segmenting apparatus may evaluate an error level based on the length of a centerline 920 of a main blob 910 among blobs indicating a target blood vessel regarding the candidate mask image 900. When the length of the centerline 920 of the main blob 910 indicating a target blood vessel in the candidate mask image 900 is equal to or less than a first threshold length, a blood vessel image segmenting apparatus may evaluate the candidate mask image 900 as an error. The first threshold length may be set differently for the area and type of target blood vessel a blood vessel image segmenting apparatus receives from a user. For example, since an LM generally has a length of 1.0 cm to 2.5 cm, the first threshold length may be set to 0.5 cm.

Hereinafter, a process of generating a target blood vessel segmentation result based on an evaluated error level of each of candidate mask images is described.

As described above, according to an embodiment, a blood vessel image segmenting apparatus may evaluate an error level for each of candidate mask images and generate a target blood vessel segmentation result using only some candidate mask images among the evaluated candidate mask images. According to an embodiment, a blood vessel image segmenting apparatus may generate a target blood vessel image segmentation result based on remaining candidate mask images after excluding a candidate mask image evaluated as an error among evaluated candidate mask images. In other words, a blood vessel image segmenting apparatus may exclude candidate mask images obviously determined as an error from candidate mask images and subsequently generate a target blood vessel segmentation result by combining remaining candidate mask images. By generating a target blood vessel segmentation result after excluding candidate mask images obviously determined as an error, a blood vessel image segmenting apparatus may more accurately segment a target blood vessel desired by a user.

According to an embodiment, a blood vessel image segmenting apparatus may generate a target blood vessel segmentation result by combining remaining candidate mask images after excluding a candidate mask image evaluated as an error, for each individual pixel.

According to an embodiment, a blood vessel image segmenting apparatus may determine for each pixel whether a pixel indicates a target blood vessel according to information indicated by the majority of candidate mask images that are not evaluated as an error. For example, for a random pixel, when the number of candidate mask images indicating the corresponding pixel as a target blood vessel is greater than the number of candidate mask images not indicating the corresponding pixel as the target blood vessel, the blood vessel image segmenting apparatus may determine that the corresponding pixel indicates the target blood vessel.

According to another embodiment, a blood vessel image segmenting apparatus may also determine for each pixel, by calculating an average of pixel values given to corresponding pixels in candidate mask images that are not evaluated as an error, whether a corresponding pixel indicates a target blood vessel. For example, for a random pixel, when an average of pixel values given to corresponding pixels in candidate mask images exceeds a threshold value, the blood vessel image segmenting apparatus may determine a corresponding pixel as a pixel indicating a target blood vessel. However, the examples described above may only be embodiments. A target blood vessel segmentation result may also be generated using remaining candidate mask images after excluding candidate mask images evaluated as an error through other various methods.

According to an embodiment, when a blood vessel image segmenting apparatus evaluates all generated candidate mask images as an obvious error, the blood vessel image segmenting apparatus may generate a target blood vessel segmentation result by selecting a candidate mask image having the lowest error level or by selecting candidate mask images having an error level equal to or below a predetermined error level among generated candidate mask images. Specifically, when the blood vessel image segmenting apparatus evaluates all generated candidate mask images as an obvious error, the blood vessel image segmenting apparatus may evaluate an error level by calculating an error score according to an individual error evaluation criterion for each of the generated candidate mask images. A specific method of calculating an error score according to an error evaluation criterion is described below. According to an embodiment, when all generated candidate mask images are evaluated as an obvious error, a blood vessel image segmenting apparatus may generate a target blood vessel segmentation result using a candidate mask image having the lowest error level. According to another embodiment, when all generated candidate mask images are evaluated as an obvious error, a blood vessel image segmenting apparatus may generate a target blood vessel segmentation result by selecting candidate mask images having an error level equal to or below a predetermined error level. For example, the blood vessel image segmenting apparatus may determine whether a pixel indicates a target blood vessel according to information indicated by the majority of the selected candidate mask images. In another example, a blood vessel image segmenting apparatus may also determine for each pixel, by calculating an average of pixel values given to corresponding pixels in the selected candidate mask images, whether a corresponding pixel indicates a target blood vessel.

On the other hand, according to another embodiment, a blood vessel image segmenting apparatus may also evaluate an error level by calculating an error score according to an individual error evaluation criterion from the beginning, rather than by determining an obvious error for each of generated candidate mask images first. Hereinafter, a process of generating a target blood vessel segmentation result by calculating an error score for each of candidate mask images is described.

A blood vessel image segmenting apparatus may evaluate an error level for each of generated candidate mask images. According to an embodiment, a blood vessel image segmenting apparatus may calculate an error score based on connectivity of pixels indicating a target blood vessel area, calculate an error score based on a blob indicating a target blood vessel, calculate an error score based on the topology of an area indicating a target blood vessel, and calculate an error score based on the length of a centerline of an area indicating a target blood vessel, for each of candidate mask images. A blood vessel image segmenting apparatus may evaluate an error level of a candidate mask image by adding error scores according to an individual error evaluation criterion regarding the candidate mask image. According to an embodiment, a blood vessel image segmenting apparatus may also evaluate an error level of a candidate mask image by giving a different weight to each error evaluation criterion and adding error scores. For example, a weight for an error score calculated based on a blob in a candidate mask image may be set higher than a weight for an error score calculated based on the topology and error scores may be added together.

A blood vessel image segmenting apparatus may determine a target blood vessel by adding error scores calculated according to an individual evaluation criterion for each of candidate mask images. According to an embodiment, a target blood vessel segmentation result may be generated using a candidate mask image having the lowest sum of error scores calculated for each error evaluation criterion among generated candidate mask images.

According to another embodiment, a target blood vessel segmentation result may be generated by combining remaining candidate mask images after excluding a candidate mask image having a sum of error scores calculated according to an individual evaluation criterion equal to or greater than a second threshold value among generated candidate mask images. For example, a blood vessel image segmenting apparatus may determine for each pixel whether a pixel indicates a target blood vessel according to information indicated by the majority of candidate mask images having a sum of error scores below a second threshold value. For example, for a random pixel, when the number of candidate mask images indicating the corresponding pixel as a target blood vessel is greater than the number of candidate mask images not indicating the corresponding pixel as the target blood vessel, a blood vessel image segmenting apparatus may determine that the corresponding pixel indicates the target blood vessel. In another example, a blood vessel image segmenting apparatus may also determine for each pixel, by calculating an average of pixel values given to corresponding pixels in candidate mask images having a sum of error scores below a second threshold value, whether a corresponding pixel indicates a target blood vessel. In other words, for a random pixel, when an average of pixel values given to corresponding pixels in candidate mask images exceeds a threshold value, a blood vessel image segmenting apparatus may determine a corresponding pixel as a pixel indicating a target blood vessel.

Figure 10:
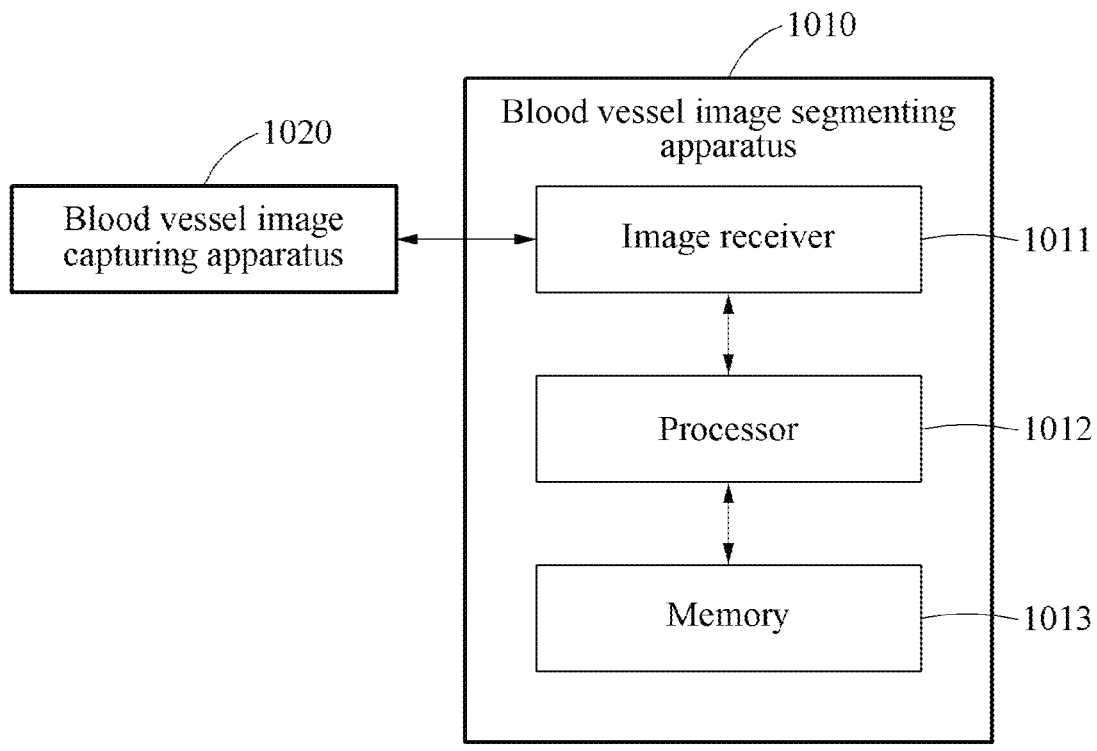
FIG. 10 is a diagram generally illustrating a blood vessel image segmemtating apparatus according to an embodiment.

FIG. 10 is a diagram generally illustrating a blood vessel image segmenting apparatus according to an embodiment.

A blood vessel image segmenting system 1000 according to an embodiment may include a blood vessel image segmenting apparatus 1010 and a blood vessel image capturing apparatus 1020. The blood vessel image segmenting apparatus 1010 may include an image receiver 1011, a processor 1012, and a memory 1013. The image receiver 1011 may receive a blood vessel image captured by the blood vessel image capturing apparatus 1020. The memory 1013 may store blood vessel segmentation models for each area and type of target blood vessel. The processor 1012 may load blood vessel segmentation models stored in the memory 1013 and generate candidate mask images from a blood vessel image received by the image receiver 1011 by applying a plurality of blood vessel segmentation models. In addition, the processor 1012 may evaluate an error level for each of generated candidate mask images and generate a target blood vessel segmentation result from the candidate mask images based on the evaluated error level. Operations of the processor 1012 is not limited to the above. The processor 1012 may perform the operations described above with reference to FIGS. 1 to 9.

The embodiments described herein may be implemented using hardware components, software components, and/or combinations thereof. For example, a device, a method, and a component described in the embodiments may be implemented using one or more general-purpose or special-purpose computers, such as, for example, a processor, a controller, an arithmetic logic unit (ALU), a digital signal processor, a microcomputer, an FPGA, a programmable logic unit (PLU), a microprocessor, or any other device capable of responding to and executing instructions in a defined manner. The processing device may run an operating system (OS) and one or more software applications that run on the OS. The processing device also may access, store, manipulate, process, and generate data in response to execution of the software. For purpose of simplicity, the description of the processing device is used as singular. However, one skilled in the art will appreciate that the processing device may include multiple processing elements and multiple types of processing elements. For example, the processing device may include multiple processors or a processor and a controller. In addition, different processing configurations are possible, such as parallel processors.

Software may include a computer program, a piece of code, an instruction, or some combination thereof, to independently or collectively instruct or configure the processing device to operate as desired. Software and/or data may be embodied permanently or temporarily in any type of machine, component, physical or virtual equipment, computer storage medium or device, or in a propagated signal wave capable of providing instructions or data to or being interpreted by the processing device. The software may also be distributed over network-coupled computer systems so that the software is stored and executed in a distributed fashion. The software and data may be stored by one or more non-transitory computer-readable recording media.

The methods according to the above-described embodiments may be recorded in non-transitory computer-readable media including program instructions to implement various operations of the above-described embodiments. The media may also include the program instructions, data files, data structures, and the like alone or in combination. The program instructions recorded on the media may be those specially designed and constructed for the purposes of embodiments, or they may be of the kind well-known and available to those having skill in the computer software arts. Examples of non-transitory computer-readable media include magnetic media such as hard disks, floppy disks, and magnetic tape; optical media such as CD-ROM discs and DVDs; magneto-optical media such as floptical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as one produced by a compiler, and higher-level code that may be executed by the computer using an interpreter.

The above-described hardware devices may be configured to act as one or more software modules in order to perform the operations of the above-described embodiments, or vice versa.

While this disclosure includes embodiments illustrated with reference to limited drawings, it will be apparent to one of ordinary skill in the art that various changes in form and details may be made in these embodiments without departing from the spirit and scope of the claims and their equivalents. Descriptions of features or aspects in each embodiment are to be considered as being applicable to similar features or aspects in other embodiments. Suitable results may be achieved if the described techniques are performed in a different order, and/or if components in a described system, architecture, device, or circuit are coupled or combined in a different manner, and/or replaced or supplemented by other components or their equivalents.

Therefore, the scope of the disclosure is defined not by the detailed description but by the claims and their equivalents, and all variations within the scope of the claims and their equivalents are to be construed as being included in the disclosure.

What is claimed is:

1. A method, performed by a processor, of segmenting a blood vessel image, the method comprising:

generating a plurality of candidate mask images regarding a target blood vessel by applying a plurality of blood vessel segmentation models to a blood vessel image;

evaluating an error level for each of the generated plurality of candidate mask images; and generating a target blood vessel segmentation result from the candidate mask images based on the evaluated error level wherein the evaluating of the error level for each of the generated plurality of candidate mask images comprises, when a number of pixels included in a blob other than a main blob in a corresponding candidate mask image is equal to or greater than a first threshold ratio compared to a number of pixels indicating a target blood vessel, evaluating the candidate mask image as an error.

2. The method of claim 1, wherein the evaluating of the error level for each of the generated plurality of candidate mask images comprises, when at least one of pixels indicating a target blood vessel area in a corresponding candidate mask image is separated, evaluating the candidate mask image as an error.

3. The method of claim 1, wherein the evaluating of the error level for each of the generated plurality of candidate mask images comprises evaluating an error level of a corresponding candidate mask image based on a topology of an area indicating the target blood vessel in the corresponding candidate mask image.

4. The method of claim 3, wherein the evaluating of the error level of the candidate mask image based on the topology of the area indicating the target blood vessel comprises, based on a trend line calculated based on diameter information of the area indicating the target blood vessel in the candidate mask image, when there is an area having diameter information equal to or greater than a second threshold ratio from the trend line within the area indicating the target blood vessel, evaluating the candidate mask image as an error.

5. The method of claim 3, wherein the evaluating of the error level of the candidate mask image based on the topology of the area indicating the target blood vessel comprises, based on a trend line calculated based on brightness information of the area indicating the target blood vessel in the candidate mask image, when there is an area having a brightness difference equal to or greater than a third threshold ratio from the trend line within the area indicating the target blood vessel, evaluating the candidate mask image as an error.

6. The method of claim 1, wherein the generating of the target blood vessel segmentation result from the candidate mask images based on the evaluated error level comprises generating a target blood vessel segmentation result based on candidate mask images obtained by excluding candidate mask images that are evaluated as errors from the plurality of candidate mask images.

7. The method of claim 6, wherein the generating of the target blood vessel segmentation result from the candidate mask images based on the evaluated error level comprises, when all of the plurality of candidate mask images are evaluated as errors, generating a target blood vessel segmentation result based on a candidate mask image having an error level equal to or less than a predetermined error level or a candidate mask image having a lowest error level.

8. The method of claim 1, wherein the evaluating of the error level for each of the generated plurality of candidate mask images comprises:

calculating an error score based on connectivity between pixels indicating a target blood vessel in a corresponding candidate mask image, calculating an error score based on a blob indicating the target blood vessel, calculating an error score based on a topology of an area indicating the target blood vessel, and calculating an error score based on a length of a centerline of the area indicating the target blood vessel.

9. A non-transitory computer-readable storage medium storing instructions that, when executed by a processor, cause the processor to perform the method of claim 1.

10. A method, performed by a processor, of segmenting a blood vessel image, the method comprising:

generating a plurality of candidate mask images regarding a target blood vessel by applying a plurality of blood vessel segmentation models to a blood vessel image;

evaluating an error level for each of the generated plurality of candidate mask images; and generating a target blood vessel segmentation result from the candidate mask images based on the evaluated error level wherein the evaluating of the error level for each of the generated plurality of candidate mask images comprises:

when a length of a centerline of an area indicating a target blood vessel in a corresponding candidate mask image is equal to or less than a first threshold length, evaluating the candidate mask image as an error, calculating an error score based on connectivity between pixels indicating a target blood vessel in a corresponding candidate mask image, calculating an error score based on a blob indicating the target blood vessel, calculating an error score based on a topology of an area indicating the target blood vessel, and calculating an error score based on a length of a centerline of the area indicating the target blood vessel.

11. An apparatus for segmenting a blood vessel image, the apparatus comprising:

an image receiver configured to receive a blood vessel image; and a processor configured to generate a plurality of candidate mask images regarding a target blood vessel by applying a plurality of blood vessel segmentation models to the blood vessel image, evaluate an error level for each of the generated plurality of candidate mask images, and generate a target blood vessel segmentation result from the candidate mask images based on the evaluated error level wherein the processor is configured to evaluate the candidate mask image as an error, when a number of pixels included in a blob other than a main blob in a corresponding candidate mask image is equal to or greater than a first threshold ratio compared to a number of pixels indicating a target blood vessel.

* * * * *